United States Patent
Takahashi

(10) Patent No.: US 8,668,685 B2
(45) Date of Patent: Mar. 11, 2014

(54) ELECTRIC OPERATION SYSTEM

(75) Inventor: Hiroyuki Takahashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 894 days.

(21) Appl. No.: 12/394,908

(22) Filed: Feb. 27, 2009

(65) Prior Publication Data

US 2009/0171351 A1    Jul. 2, 2009

Related U.S. Application Data

(60) Division of application No. 11/111,607, filed on Apr. 21, 2005, now abandoned, which is a continuation of application No. PCT/JP03/13466, filed on Oct. 22, 2003.

(30) Foreign Application Priority Data

Oct. 23, 2002  (JP) ................................. 2002-308691

(51) Int. Cl.
*A61B 18/10*    (2006.01)
*A61B 18/14*    (2006.01)

(52) U.S. Cl.
USPC .............................................. 606/34; 606/41

(58) Field of Classification Search
USPC .................... 606/1, 32, 34, 41, 42
See application file for complete search history.

(56) References Cited

U.S. PATENT DOCUMENTS

| | | | |
|---|---|---|---|
| 4,846,196 A * | 7/1989 | Wiksell et al. | ............... 607/99 |
| 5,455,766 A | 10/1995 | Scheller et al. | |
| 5,836,897 A | 11/1998 | Sakurai et al. | |
| 5,947,729 A | 9/1999 | Bell | |
| 6,251,113 B1 | 6/2001 | Appelbaum et al. | |
| 6,480,762 B1 | 11/2002 | Uchikubo et al. | |
| 6,652,514 B2 | 11/2003 | Ellman et al. | |
| 6,666,860 B1 | 12/2003 | Takahashi | |
| 6,758,842 B2 | 7/2004 | Irion et al. | |
| 7,135,029 B2 | 11/2006 | Makin et al. | |
| 2001/0034532 A1* | 10/2001 | Cimino | ............... 606/169 |
| 2002/0009015 A1* | 1/2002 | Laugharn et al. | ............... 366/108 |
| 2002/0038102 A1 | 3/2002 | McFarlin et al. | |
| 2002/0087179 A1 | 7/2002 | Culp et al. | |
| 2002/0165469 A1* | 11/2002 | Murakami | ............... 601/2 |

(Continued)

FOREIGN PATENT DOCUMENTS

| | | |
|---|---|---|
| JP | 64-67286 | 3/1989 |
| JP | 09-248308 | 9/1997 |

(Continued)

*Primary Examiner* — Michael Peffley
(74) *Attorney, Agent, or Firm* — Scully, Scott, Murphy & Presser, P.C.

(57) ABSTRACT

When a treatment instrument is connected to the corresponding device (electric scalpel device or ultrasonic wave generation device), the device (electric scalpel device or ultrasonic wave generation device) transmits information related to the type, mode, and setting of the treatment instrument to a system controller. Accordingly, if a new treatment instrument is used, the system controller can perform display information related to the new treatment instrument and control the new treatment instrument. Even when the system controller is used in combination with newly-developed electric cautery knife and other treatment instruments, the system controller can obtain fixed information related to the respective medical instruments, thus increasing the operationality. Even if wrong setting is performed outside the ratings of the instruments in the system controller, the instruments can be prevented from damage such as dielectric breakdown on the basis of the obtained fixed information.

11 Claims, 9 Drawing Sheets

(56) References Cited

U.S. PATENT DOCUMENTS

| | | |
|---|---|---|
| 2002/0165558 A1 | 11/2002 | Engel |
| 2002/0198519 A1 | 12/2002 | Qin et al. |
| 2003/0050633 A1 | 3/2003 | Ellman et al. |
| 2003/0055409 A1 | 3/2003 | Brock |
| 2003/0073981 A1 | 4/2003 | Whitman et al. |
| 2003/0093103 A1 | 5/2003 | Malackowski et al. |

FOREIGN PATENT DOCUMENTS

| | | |
|---|---|---|
| JP | 2000-032151 | 1/2000 |
| JP | 2000-254142 | 9/2000 |
| JP | 2001-166958 | 6/2001 |
| JP | 2001-178734 | 7/2001 |
| JP | 2002-182880 | 6/2002 |
| WO | WO 98/06338 | 2/1998 |

\* cited by examiner

FIG.6

| | TRANSMISSION DATA FROM ELECTRIC SCALPEL DEVICE | | |
|---|---|---|---|
| | TYPE OF TREATMENT INSTRUMENT | MONOPOLAR/ BIPOLAR | PERMISSIBLE MODE (INCISION/ COAGULATION) | ALLOWABLE OUTPUT RANGE |
| MONOPOLAR TREATMENT INSTRUMENT | INSTRUMENT ID | MONOPOLAR | INCISION AND COAGULATION | INCISION: 0~150W COAGULATION: 0~80W |
| BIPOLAR TREATMENT INSTRUMENT | INSTRUMENT ID | BIPOLAR | COAGULATION | COAGULATION: 0~100W |

FIG.7

| | | | TRANSMISSION DATA FROM ULTRASONIC WAVE GENERATION DEVICE | | | |
|---|---|---|---|---|---|---|
| | TYPE OF TREATMENT INSTRUMENT | OUTPUT MODE | ASSOCIATION/NON-ASSOCIATION WITH WATER-SUPPLY AND SUCTION DEVICE | SET RANGE OF ULTRASONIC WAVE OUTPUT | SET RANGE OF WATER SUPPLY | SET RANGE OF SUCTION |
| TREATMENT INSTRUMENT FOR INCISION AND COAGULATION | INSTRUMENT ID | SINE WAVE OUTPUT | NON-ASSOCIATION | 0~100% | — | — |
| TREATMENT INSTRUMENT FOR ULTRASONIC WAVE SUCTION | INSTRUMENT ID | SINE WAVE OUTPUT | ASSOCIATION | 0~80% | 30~100% | 0~100% |
| TREATMENT INSTRUMENT FOR LITHOTRIPSY | INSTRUMENT ID | MODULATED OUTPUT | ASSOCIATION | 0~50% | 0~100% | 0~100% |

ELECTRIC OPERATION SYSTEM

CROSS REFERENCE TO RELATED APPLICATION

This application is a divisional application of U.S. patent application Ser. No. 11/111,607 filed on Apr. 21, 2005, now abandoned, which is a continuation application of PCT/JP03/13466 filed on Oct. 22, 2003 and claims the benefit of Japanese Application No. 2002-308691 filed in Japan on Oct. 23, 2002, the entire contents of each of which are incorporated herein by their reference.

BACKGROUND OF THE INVENTION

1. Field of the Invention

The present invention relates to an electric operation system for electric therapeutic treatment.

2. Related Art Statement

In recent years, electric treatment devices such as electric scalpel devices for supplying a high-frequency current for therapeutic treatment and ultrasonic treatment devices for therapeutic treatment using ultrasonic waves have been widespread.

For example, Japanese Unexamined Patent Application Publication No. 2000-254142 discloses an electric surgical operating apparatus. To prevent dielectric breakdown in each treatment instrument, the rated voltage of each instrument is input to the electric surgical operating apparatus so that an output voltage thereof is equal to or lower than the rated voltage of the instrument.

Japanese Unexamined Patent Application Publication No. 64-67286 discloses a method for generating ultrasonic waves with modulated frequency/amplitude. The method is suitable for ultrasonic operating apparatuses, particularly, a lithotripter.

Japanese Unexamined Patent Application Publication No. 2001-166958 discloses a system in which a program stored in a medical instrument can be rewritten or updated by an external remote-controlled computer through a communication line.

In a system controller connected to a plurality of medical devices in an electric surgical operating apparatus, treatment instruments are determined and, after that, the respective medical devices can be automatically set, thus increasing the operationality. However, it is necessary to previously input fixed information related to the respective medical devices to the system controller. To make the respective medical devices compatible with new treatment instruments, or when various modes are added to the medical devices, the system controller requires a version upgrade as the occasion arises. Disadvantageously, known electric surgical operation systems always need maintenance.

The present invention is made in consideration of the above circumstances. It is an object of the present invention to provide a flexible and secure electric operation system. According to the system of the present invention, if newly-developed electric cautery knife and other treatment instruments are used in combination with a system controller of the system, the system controller can obtain fixed information related to respective medical devices, thus increasing the operationality. When wrong setting is performed outside the rating of the respective treatment instruments in the system controller, the instruments can be prevented from damage such as dielectric breakdown on the basis of the obtained fixed information.

SUMMARY OF THE INVENTION

The present invention provides an electric operation system having one or a plurality of electric treatment instruments for treating tissue of a living body, an instrument driver connected to the electric treatment instruments, and a system controller for controlling the instrument driver, the system including: reading means for reading a plurality of operation parameters of the electric treatment instruments connected to the instrument driver; and control-parameter-range determining means for determining a control parameter range, where the instrument driver is controllable by the system controller, on the basis of the operation parameters read by the reading means.

Other features and advantages of the present invention will become more apparent from the following description.

BRIEF DESCRIPTION OF THE DRAWINGS

FIGS. 1 to 9 relate to an embodiment of the present invention;

FIG. 1 shows the structure of an electric surgical operation system;

FIG. 2 is a block diagram showing the structure of an electric scalpel device in FIG. 1;

FIG. 3 is a block diagram of the structure of an ultrasonic wave generation device;

FIG. 4 is a block diagram showing the structure of a water-supply and suction device in FIG. 1;

FIG. 5 is a block diagram showing the structure of a system controller in FIG. 1;

FIG. 6 is a diagram showing the structure of transmission data indicating the type of each treatment instrument connected to and determined by the electric scalpel device in FIG. 1;

FIG. 7 is a diagram showing the structure of transmission data indicating the type of each treatment instrument connected to and determined by the ultrasonic wave generation device in FIG. 1;

FIG. 8 is a first flowchart explaining the operation of the electric surgical operation system in FIG. 1; and FIG. 9 is a second flowchart explaining the operation of the electric surgical operation system in FIG. 1.

DETAILED DESCRIPTION OF THE PREFERRED EMBODIMENT(S)

To describe the present invention in farther detail, the present invention will now be explained with reference to the accompanying drawings.

Figure 1:
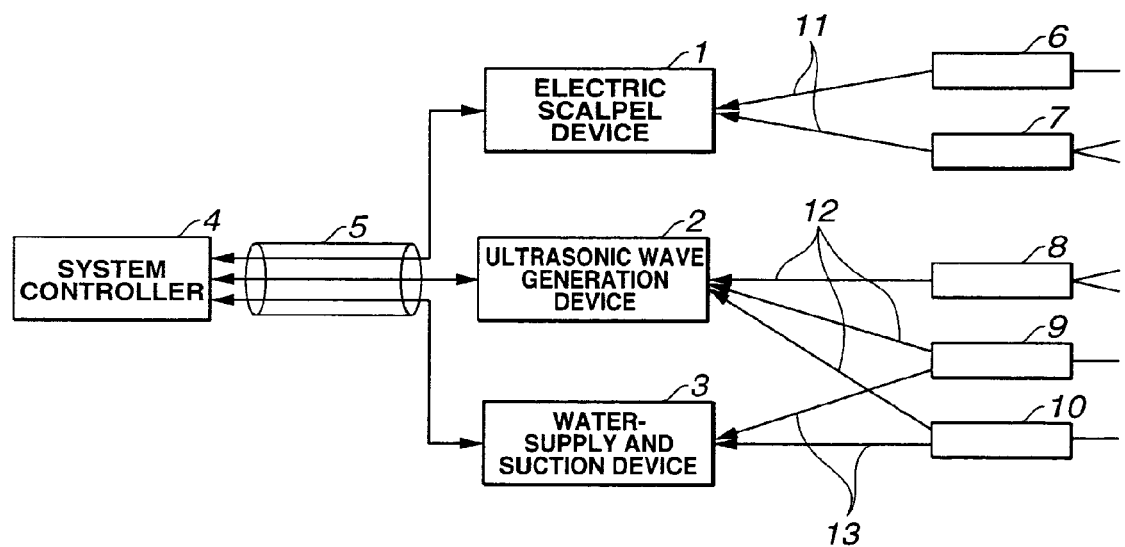

According to an embodiment of the present invention, referring to FIG. 1, an electric surgical operation system includes an electric scalpel device 1, an ultrasonic wave generation device 2, a water-supply and suction device 3, and a system controller 4. The electric scalpel device 1, the ultrasonic wave generation device 2, and the water-supply and suction device 3 are connected to the system controller 4 via a communication cable 5. Each device transmits and receives status information and control information to/from the system controller 4.

A monopolar treatment instrument 6 and a bipolar treatment instrument 7 are selectively connected to the electric scalpel device 1 via electric scalpel cords 11. The electric scalpel device 1 is used to incise and coagulate tissue by applying electric power to the tissue from the distal end of the treatment instrument.

A treatment instrument 8 for incision and coagulation, a treatment instrument 9 for ultrasonic wave suction, and a treatment instrument 10 for lithotripsy are selectively connected to the ultrasonic wave generation device 2 via ultrasonic cables 12. The ultrasonic wave generation device 2 is used to incise and coagulate tissue, emulsify tissue and suck the emulsified tissue, or crush a stone into pieces and suck the pieces by generating ultrasonic waves from the distal end of the treatment instrument.

The treatment instrument 9 for ultrasonic wave suction and the treatment instrument 10 for lithotripsy are selectively connected to the water-supply and suction device 3 via water-supply and suction tubes 13. The water-supply and suction device 3 allows the distal end of the treatment instrument to supply wash water. In addition, the water-supply and suction device 3 is used to suck the emulsified tissue or the crushed stone pieces.

Figure 2:
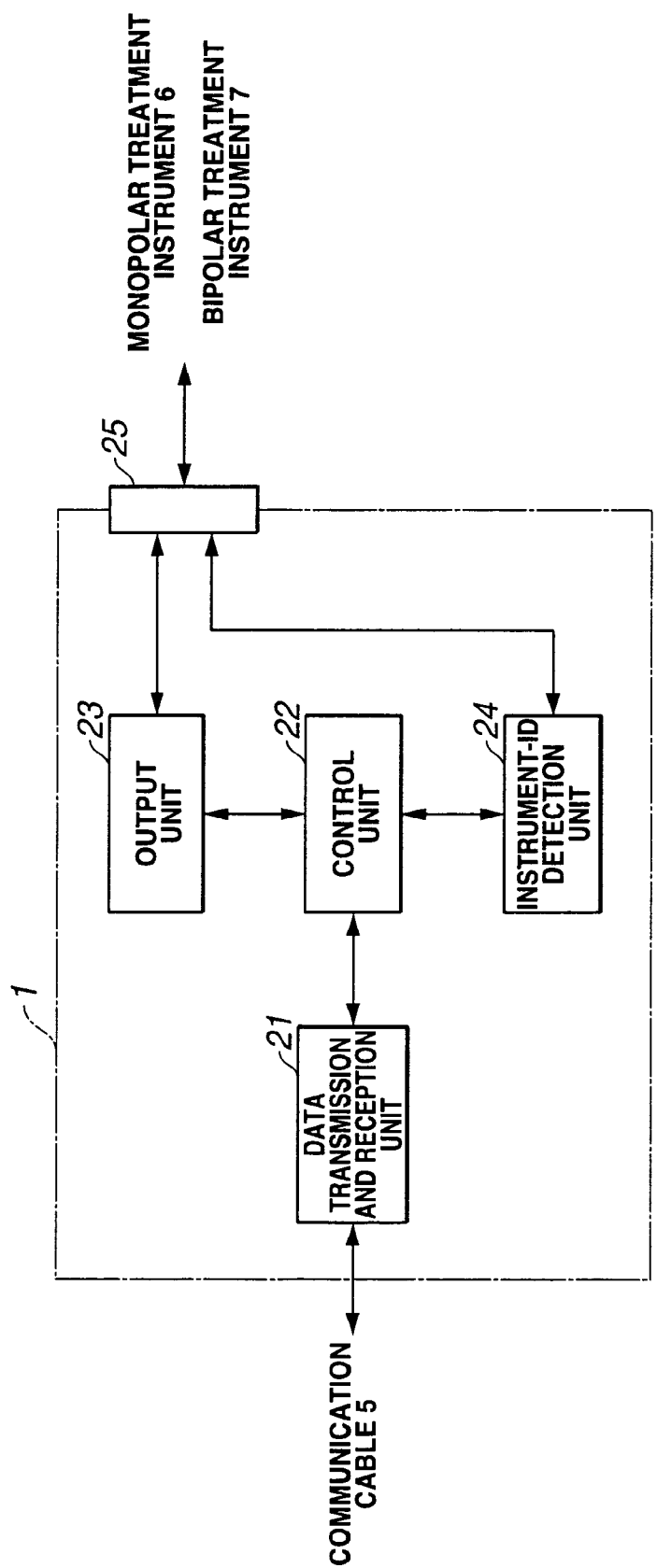

Referring to FIG. 2, the electric scalpel device 1 includes: a connector 25 which is connected to an electric cord 11 of the monopolar treatment instrument 6 or the bipolar treatment instrument 7; an instrument-ID detection unit 24 for detecting ID assigned to the treatment instrument connected to the connector 25; an output unit 23 for supplying a high-frequency current for treatment to the treatment instrument through the connector 25; a control unit 22 for controlling the high-frequency current generated from the output unit 23; and a data transmission and reception unit 21 used for communication between the control unit 22 and the system controller 4, namely, for transmitting instrument-ID information generated from the instrument-ID detection unit 24 and control information of the output unit 23.

Figure 3:
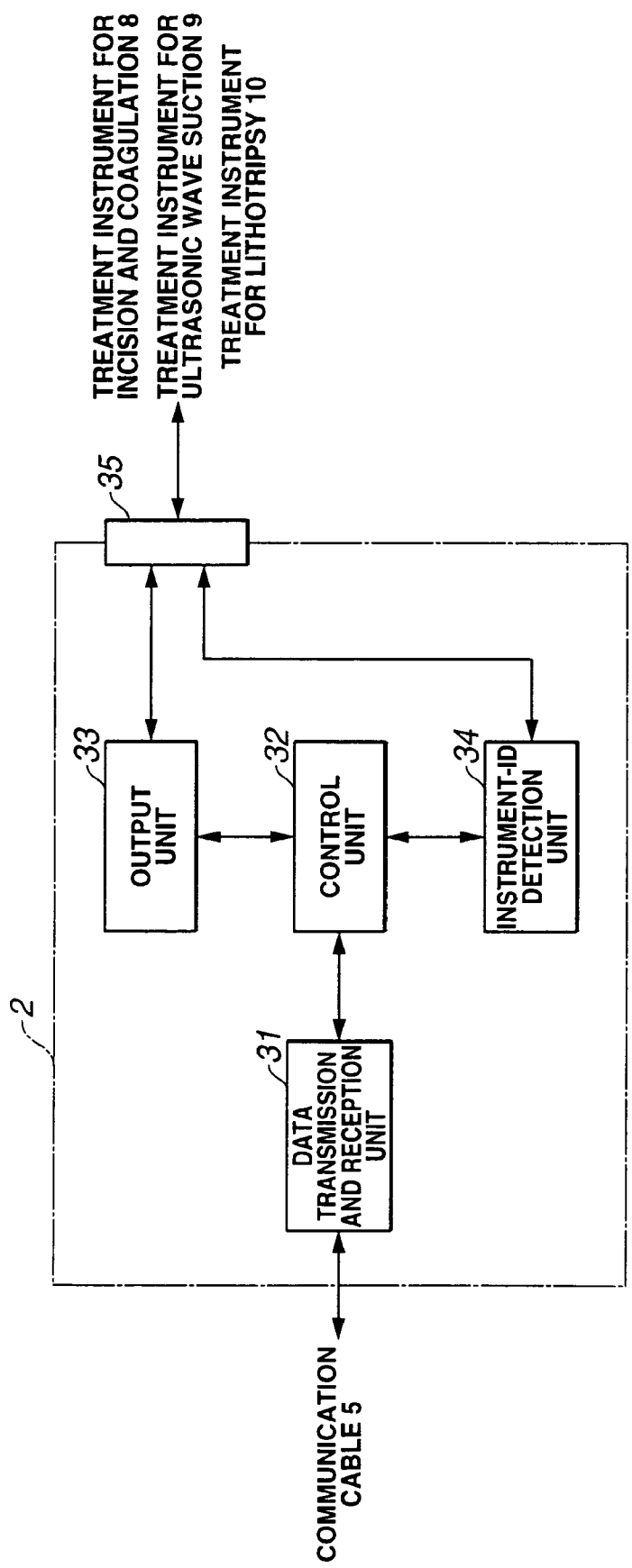

Referring to FIG. 3, the ultrasonic wave generation device 2 includes: a connector 35 which is connected to the ultrasonic cable 12 of the treatment instrument 8 for incision and coagulation, the treatment instrument 9 for ultrasonic wave suction, or the treatment instrument 10 for lithotripsy; an instrument-ID detection unit 34 for detecting ID assigned to the treatment instrument connected to the connector 35; an output unit 33 for generating a drive signal to an ultrasonic vibrator provided for the treatment instrument through the connector 35; a control unit 32 for controlling the drive signal generated by the output unit 33; and a data transmission and reception unit 31 used for communication between the control unit 32 and the system controller 4, namely, for transmitting instrument-ID information generated from the instrument-ID detection unit 34 and control information of the output unit 23.

Figure 4:
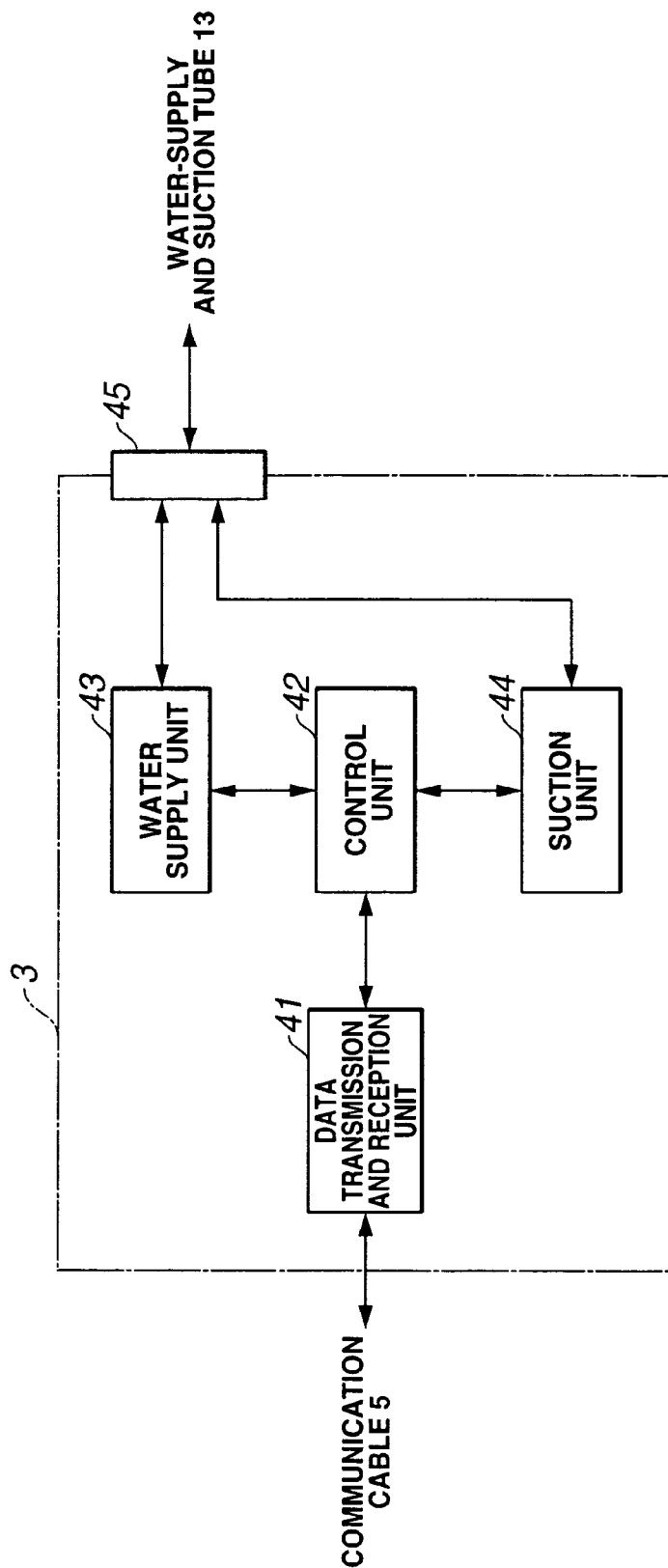

Referring to FIG. 4, the water-supply and suction device 3 includes: a connector 45 which is connected to the water-supply and suction tube 13 of the treatment instrument 9 for ultrasonic wave suction or the treatment instrument 10 for lithotripsy; a water supply unit 43 for supplying water to the treatment instrument through the connector 45; a suction unit 44 for allowing the treatment instrument to perform suction via the connector 45; a control unit 42 for controlling the water supply unit 43 and the suction unit 44; and a data transmission and reception unit 41 used for communication between the control unit 42 and the system controller 4, namely, for transmitting control information of the water supply unit 43 and the suction unit 44.

Figure 5:
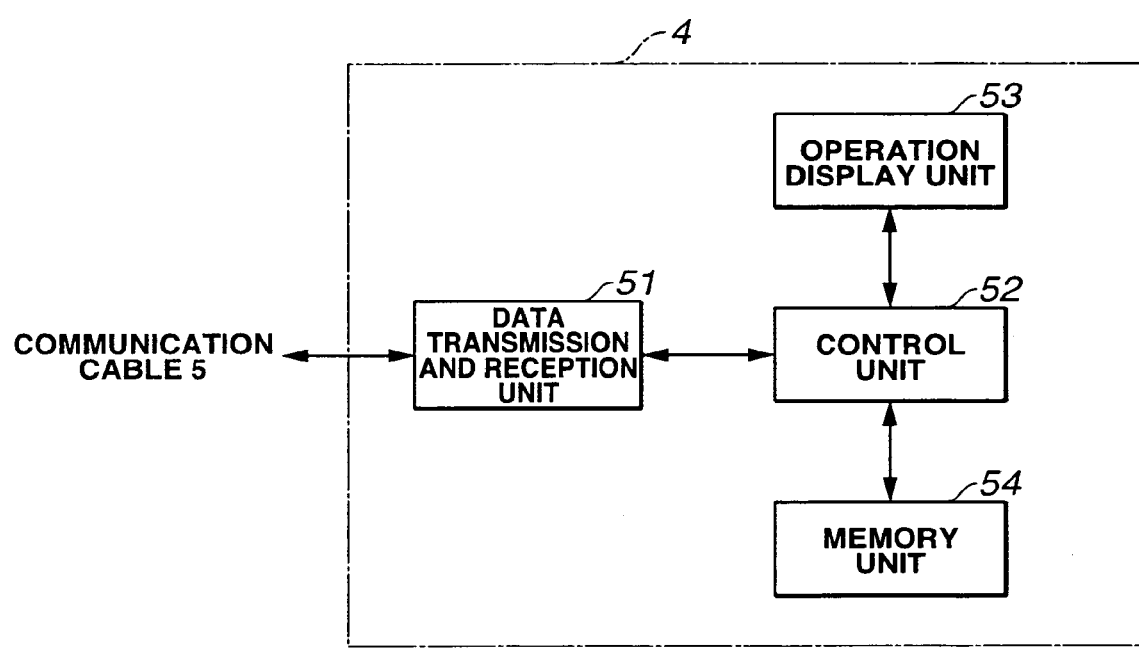

Referring to FIG. 5, the system controller 4 includes: an operation display unit 53 for displaying an operation screen to operate the electric scalpel device 1, the ultrasonic wave generation device 2, and the water-supply and suction device 3, the unit 53 having a touch panel function through which operation instruction information can be entered on the displayed operation screen; a memory unit 54 for storing data such as operation parameters of the electric scalpel device 1, the ultrasonic wave generation device 2, and the water-supply and suction device 3 and control commands and a control program; a control unit 52 for centrally controlling the respective devices by executing the stored control program; and a data transmission and reception unit 51 for communicating with the data transmission and reception units 21, 31, and 41. The system controller 4 permits the operation display unit 53 to display the operation, mode, and a programmed output of each of the electric scalpel device 1, the ultrasonic wave generation device 2, and the water-supply and suction device 3.

Features according to the present embodiment will now be described below. As endoscopic surgery recently becomes more advanced, precise treatment instruments are developed. The structures of the instruments are precise. In the use of the treatment instruments, therefore, it is necessary to set lower power of the electric scalpel device and the ultrasonic wave generation device than the rated values of the respective devices. If the power is set higher than the rating and is then generated from the corresponding treatment instrument, the instrument may be damaged.

To overcome the above-mentioned disadvantage, conventionally, each device determines the type of treatment instrument and then defines an output mode suited to the instrument and the upper limit of set output. This situation is not shown.

However, since any known controller can operate respective devices, the types of treatment instruments are previously stored in a memory of the controller. When any treatment instrument is connected to any device, set information corresponding to the treatment instrument can be read from the memory and be displayed. Thus, the connected instrument can be controlled.

When a treatment instrument is newly developed after the system controller is developed, therefore, it is necessary to upgrade the memory of the system controller to a recent version because the type of the corresponding treatment instrument and set information thereof are not stored in the memory.

According to the features of the present embodiment, when a treatment instrument is connected to the device (electric scalpel device 1 or ultrasonic wave generation device 2), the device (electric scalpel device 1 or ultrasonic wave generation device 2) transmits the type of treatment instrument, the mode, and set information thereof to the system controller 4. Thus, the system controller 4 can permit display of the set information and control the new treatment instrument.

Figure 8:
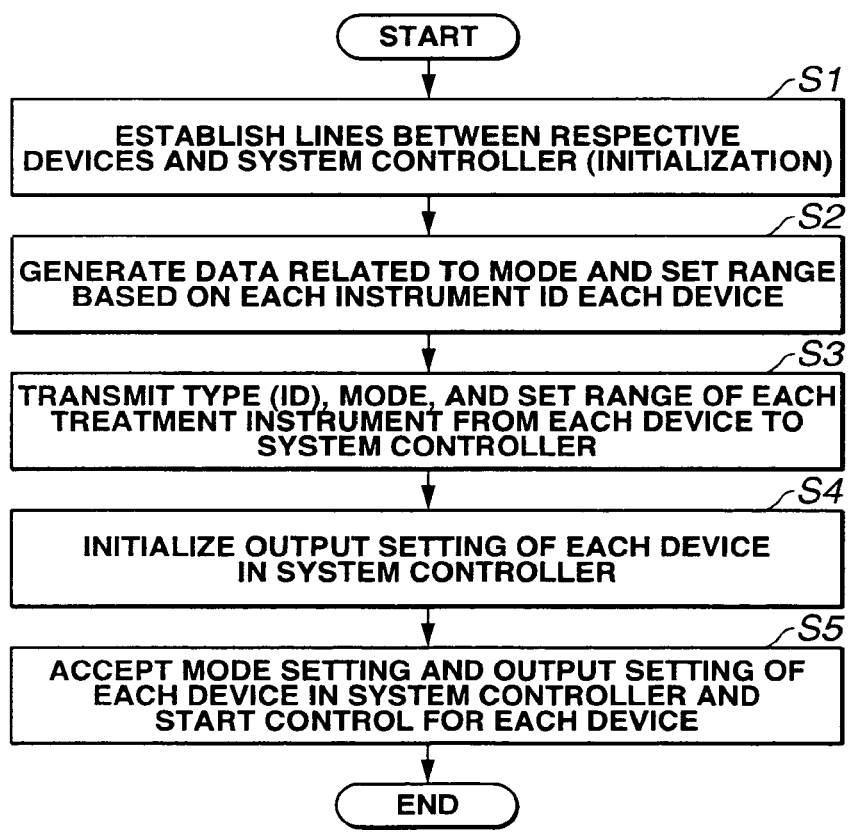

For details, referring to FIG. 8, in step S1, communication lines are established between the respective devices (the electric scalpel device 1 and the ultrasonic wave generation device 2) and the system controller 4. In step S2, each of the devices (electric scalpel device 1 and ultrasonic wave generation device 2) generates data related to the type (ID), mode, and set range of each treatment instrument. In step S3, the data related to the type (ID), mode, and set range of each treatment instrument connected to each of the devices (electric scalpel device 1 and ultrasonic wave generation device 2) is transmitted to the system controller 4 from each of the devices (electric scalpel device 1 and ultrasonic wave generation device 2). In step S4, the transmission data is stored to the memory unit 54 in the system controller 4, thus initializing a set output value of each of the devices (electric scalpel device 1 and ultrasonic wave generation device 2). In step S5, the system controller 4 accepts mode setting and output setting related to the devices (electric scalpel device 1 and ultrasonic wave generation device 2) entered by a user and then starts the control of the devices (electric scalpel device 1 and ultrasonic wave generation device 2). Then, the process terminates.

(1) Case of Electric Scalpel Device 1

For example, a newly-developed monopolar treatment instrument 6 or bipolar treatment instrument 7 is connected to the electric scalpel device 1.

The electric scalpel device 1 determines the type of the connected treatment instrument and then transmits data to the system controller 4. For example, referring to FIG. 6, the transmission data includes instrument-ID data used to determine the type of treatment instrument, monopolar/bipolar type data, permissible-mode (incision/coagulation) data, and data indicating an allowable output range.

To take the case of FIG. 6 as an example, when the monopolar treatment instrument 6 is connected to the electric scalpel device 1, the following transmission data is transmitted.

(1-1) Monopolar Treatment Instrument 6:

Instrument-ID data=treatment instrument ID, monopolar/bipolar type data=monopolar, permissible-mode (incision/coagulation) data=incision and coagulation, allowable-output-range data=incision at 0 to 150 W and coagulation at 0 to 80 W.

(1-2) Bipolar Treatment Instrument 7:

Instrument-ID data=treatment instrument ID, monopolar/bipolar type data=bipolar, permissible-mode (incision/coagulation) data=coagulation, allowable-output-range data=coagulation at 0 to 100 W.

(2) Case of Ultrasonic Wave Generation Device 2

The ultrasonic wave generation device 2 is operatively associated with the water-supply and suction device 3 depending on a treatment instrument that is used.

For example, a newly-developed treatment instrument 8 for incision and coagulation, treatment instrument 9 for ultrasonic wave suction, or treatment instrument 10 for lithotripsy is connected to the ultrasonic wave generation device 2.

The ultrasonic wave generation device 2 determines the type of treatment instrument connected thereto and then transmits data to the system controller 4. For example, referring to FIG. 7, the transmission data includes instrument-ID data used to determine the type of treatment instrument, monopolar/bipolar type data, output mode data, association/non-association data indicating whether the present device is operatively associated with the water-supply and suction device 3 or not, data indicating the set range of ultrasonic output, data indicating the set range of water supply, and data indicating the set range of suction.

To take the case of FIG. 7 as an example, when the treatment instrument 8 for incision and coagulation is connected to the ultrasonic wave generation device 2, the following transmission data is transmitted.

The upper limit of set output of each treatment instrument connected to the ultrasonic wave generation device 2 is determined on the basis of the shape of the distal end of the instrument and the amplitude at the distal end thereof. For example, when the treatment instrument is narrow, stress strain caused by ultrasonic vibration at the distal end of the instrument is large. Thus, allowable amplitude is small.

(2-1) Treatment Instrument 8 for Incision and Coagulation:

Instrument-ID data=treatment instrument ID, output mode data sine wave output, data indicating the association/non-association with the water-supply and suction device 3=non-association, ultrasonic-output set range data=ultrasonic output from 0 to 100%.

(2-2) Treatment Instrument 9 for Ultrasonic Wave Suction:

Instrument-ID data=treatment instrument ID, output mode data=sine wave output, data indicating the association/non-association with the water-supply and suction device 3=association, ultrasonic-output set range data=ultrasonic output from 0 to 80%, water-supply set range data=water supply from 30 to 100%, and suction set range data suction from 0 to 100%.

In this instance, in the treatment instrument 9 for ultrasonic wave suction, water supply is performed not only for washing tissue but also for lowering heat generated by ultrasonic vibration of the treatment instrument. Therefore, the settable rate of water supply is not from 0%.

Accordingly, the lowest allowable rate of water supply is defined depending on ultrasonic setting. Control is performed so that the rate of water supply is not set equal to or lower than the lowest rate.

Figure 9:
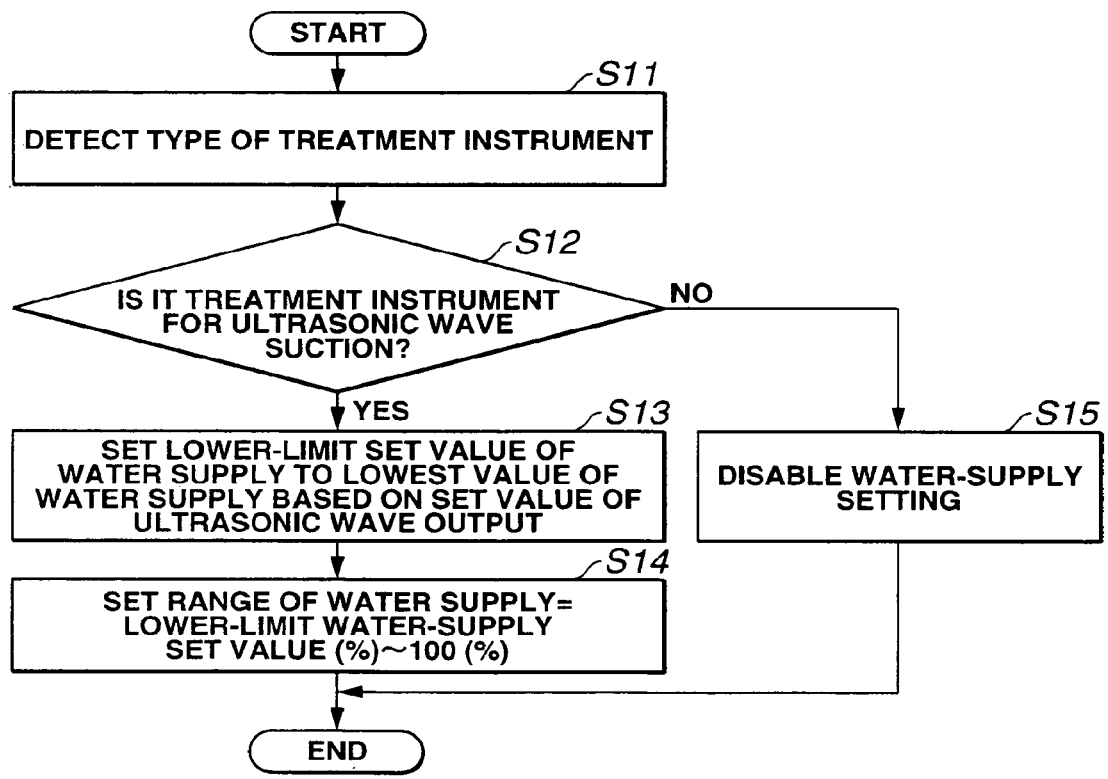

In other words, referring to FIG. 9, in the ultrasonic wave generation device 2, the type of treatment instrument connected thereto is detected in step S11. In step S12, whether the connected treatment instrument is the treatment instrument 9 for ultrasonic wave suction or not is determined. If it is the treatment instrument 9 for ultrasonic wave suction, in step S13, the lower-limit set value of water supply is set to the lowest value of water supply calculated on the basis of the set value of ultrasonic output. In step S14, the set rage of water supply is set from the lower-limit water-supply set value (%) to 100(%). Then, the process terminates. When it is determined in step S12 that the treatment instrument is not the treatment instrument 9 for ultrasonic wave suction, in step S15, water-supply setting is disabled. The range of water supply is set from 0(%) to 100(%). Then, the process terminates.

Prior to setting the rate of water supply of the water-supply and suction device, this process gives higher priority to the parameter indicating the lowest rate of water supply of the treatment instrument 9 for ultrasonic wave suction. The rate of water supply must be set so as to satisfy the lowest rate. The above-mentioned case, where high priority is given to a predetermined operation parameter, is not peculiar to the present embodiment.

When the treatment instrument 9 for ultrasonic wave suction is used as mentioned above, the set range of the water-supply and suction device 3 is restricted due to setting (the set value of ultrasonic output) of another device (ultrasonic wave generation device 2).

(2-3) Treatment Instrument 10 for Lithotripsy:

Instrument-ID data=treatment instrument ID, output mode data=modulated output, data indicating the association/non-association with the water-supply and suction device 3=association, ultrasonic-output set range data=ultrasonic output from 0 to 50%, water-supply set range data=water supply from 0 to 100%, and suction set range data suction from 0 to 100%.

In this instance, for the output mode data included in transmission data, in the case of using the treatment instrument 8 for incision and coagulation and the treatment instrument 9 for suction, the output mode is set to sine wave output. Subsequent to the operation for tissue, generally, continuous ultrasonic power is applied to the tissue. Thus, desired effects can be obtained. On the other hand, when the treatment instrument 10 for lithotripsy is used, the output mode data is set to modulated output, thus transversely vibrating the distal end of the treatment instrument. It has been shown that the transverse vibration results in an increase in capability of breaking a stone. Generally, modulated ultrasonic power is sent to the treatment instrument, so that longitudinal and transverse vibrations are applied to a stone. Thus, desired effects can be obtained.

For the association/non-association with the water-supply and suction device 3, when the treatment instrument 9 for ultrasonic wave suction is used, generally, emulsified tissue and blood are sucked while tissue is being washed. Accordingly, water-supply and suction are operatively associated with ultrasonic wave generation. Thus, the treatment instrument 9 for ultrasonic wave suction is operatively associated with the device 3. In the use of the treatment instrument 10 for lithotripsy, a urinary tract or a renal cavity is filled with washing water, a stone is crushed into fragments, and the fragments are sucked. Accordingly, the treatment instrument 10 for lithotripsy is also operatively associated with the water-supply and suction device 3. The water-supply and suction device 3 sets the rate of supply of the washing water and the rate of suction.

Since the present system has the above-mentioned structure and operation, if the system controller is used in combination with newly-developed electric cautery knife and other treatment instruments, the present system is flexibly compatible with the newly-developed instruments, thus increasing the operationality. If wrong setting is performed outside the ratings of the treatment instruments in the system controller, the treatment instruments can be prevented from damage such as dielectric breakdown.

In the above-mentioned structure, after each treatment instrument is connected to each corresponding device, each device determines the type of treatment instrument connected thereto and then transmits permissible mode and output range on the basis of the type to the system controller. Recent memories are reduced in size. Accordingly, the following configuration may be used: A memory is mounted on the treatment instrument and the data is written in the memory. The treatment instrument transmits the data to the corresponding device and the system controller. Control can be performed on the basis of the data. In this case, as for the change in the entire configuration, the memory is placed in each treatment instrument as different from the foregoing case where each device determines the type of treatment instrument and stores various parameters.

The present invention is not limited to the above-mentioned embodiment but many modifications and variations are possible within the purview of the invention without departing from the spirit of the invention.

In the present invention, it will be apparent that a wide range of different embodiments can be formed based on this invention without departing from the spirit and scope of this invention. This invention will be restricted to the appended claims but not be limited to any particular embodiment.

What is claimed is:

1. An electric operation system comprising:
   at least one electric treatment instrument for therapeutically treating tissue of a living body;
   a plurality of instrument drivers connected to the at least one electric treatment instrument;
   a system controller for controlling the plurality of instrument drivers;
   a reader for reading a plurality of operation parameters of the at least one electric treatment instrument connected to the plurality of instrument drivers; and
   a control parameter range determining section for determining a control parameter range, where the plurality of instrument drivers are controllable by the system controller, on the basis of the plurality of operation parameters read by the reader, wherein
   the at least one electric treatment instrument is driven by a first instrument driver and a second instrument driver of the plurality of instrument drivers, and
   the control parameter range determining section gives a high priority to a specific operation parameter when the operation parameters of the electric treatment instrument connected to the plurality of instrument drivers are set, and sets a range of the specific operation parameter to which the high priority is given on the basis of information from the second instrument driver other than the first instrument driver corresponding to the specific operation parameter.

2. The electric operation system according to claim 1, wherein the instrument driver includes an electric scalpel device.

3. The electric operation system according to claim 2, wherein the electric treatment instrument includes a monopolar treatment instrument.

4. The electric operation system according to claim 2, wherein the electric treatment instrument includes a bipolar treatment instrument.

5. The electric operation system according to claim 1, wherein the first instrument driver includes a water supply and suction device and the second instrument driver includes an ultrasonic wave generation device.

6. The electric operation system according to claim 5, wherein the electric treatment instrument includes a treatment instrument for incision and coagulation.

7. The electric operation system according to claim 5, wherein the at least one electric treatment instrument includes a treatment instrument for lithotripsy.

8. The electric operation system according to claim 7, further comprising:
   a water-supply and suction device.

9. The electric operation system according to claim 5, wherein the at least one electric treatment instrument includes a treatment instrument for ultrasonic wave suction.

10. The electric operation system according to claim 9, further comprising:
    a water-supply and suction device.

11. The electric operation system according to claim 1, wherein the control parameter range determining section determines a control range of the specific operation parameter among the plurality of operation parameters based on a type of the electric treatment instrument connected to the first instrument driver and one or more set values of the plurality of operation parameters other than the specific operation parameter.

* * * * *